(12) United States Patent
Bromberg et al.

(10) Patent No.: US 9,514,338 B1
(45) Date of Patent: Dec. 6, 2016

(54) IMPLANTABLE IDENTIFICATION APPARATUS AND RELATED METHODS OF USE

(71) Applicants: Anne Bromberg, Birmingham, AL (US); John S. Slaven, Huntsville, AL (US)

(72) Inventors: Anne Bromberg, Birmingham, AL (US); John S. Slaven, Huntsville, AL (US)

( * ) Notice: Subject to any disclaimer, the term of this patent is extended or adjusted under 35 U.S.C. 154(b) by 0 days.

(21) Appl. No.: 14/686,356

(22) Filed: Apr. 14, 2015

Related U.S. Application Data

(60) Provisional application No. 61/979,736, filed on Apr. 15, 2014.

(51) Int. Cl.
  *G06K 7/02* (2006.01)
  *H04B 11/00* (2006.01)
  *H04L 29/08* (2006.01)
  *G06K 19/06* (2006.01)

(52) U.S. Cl.
  CPC .......... *G06K 7/02* (2013.01); *G06K 19/06* (2013.01); *H04B 11/00* (2013.01); *H04L 67/10* (2013.01)

(58) Field of Classification Search
  CPC ....... G07F 7/1008; G06Q 20/341; G06K 7/02; G05B 19/44
  USPC ......................................... 235/380, 382, 452
  See application file for complete search history.

(56) References Cited

U.S. PATENT DOCUMENTS

| 5,861,018 | A | 1/1999 | Feierbach |
| 7,525,426 | B2 | 4/2009 | Edelstein et al. |
| 7,750,810 | B2 | 7/2010 | Ritter et al. |
| 2007/0066891 | A1 | 3/2007 | Fuisz |
| 2007/0135711 | A1* | 6/2007 | Chernomorsky ...... A61B 19/54 |
| | | | 600/431 |
| 2007/0139187 | A1 | 6/2007 | Dobosz |
| 2010/0194541 | A1* | 8/2010 | Stevenson ............ A61B 5/0031 |
| | | | 340/10.1 |
| 2011/0275930 | A1 | 11/2011 | Jho et al. |

FOREIGN PATENT DOCUMENTS

WO  97/31331 A1  8/1997

\* cited by examiner

*Primary Examiner* — Karl D Frech
(74) *Attorney, Agent, or Firm* — Bush Intellectual Property Law; Kenneth M. Bush

(57) ABSTRACT

The apparatus includes information linked to a person by data encoded in a texture. The texture has a pattern, and the texture is formed upon a chip implantable within the person. The pattern may be resolvable by an ultrasound scanner into a pattern image that is computer readable to extract the data from the image when the chip is implanted within the person. The related methods include the step of encoding data upon a chip by forming a pattern with a texture, the data being linked to an identity of the person, and the step of implanting the chip. The methods may include the steps of scanning the implanted chip to obtain a pattern image using an ultrasound scanner, extracting data from the pattern image, and displaying information linked to the person by the data encoded in the pattern, the information residing in a remote database.

13 Claims, 3 Drawing Sheets

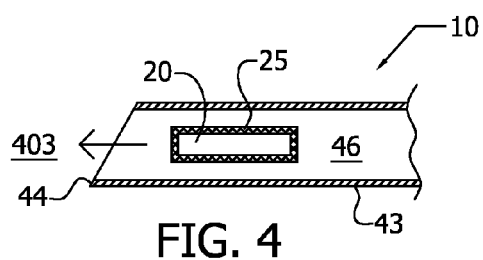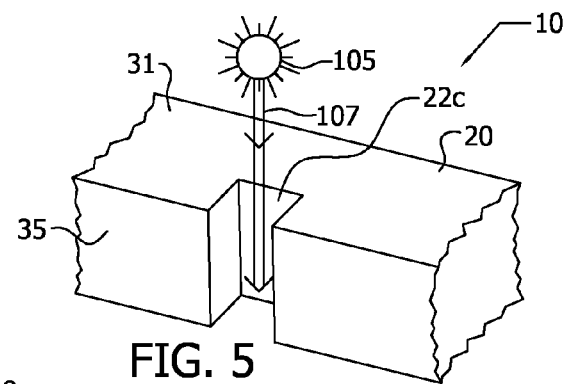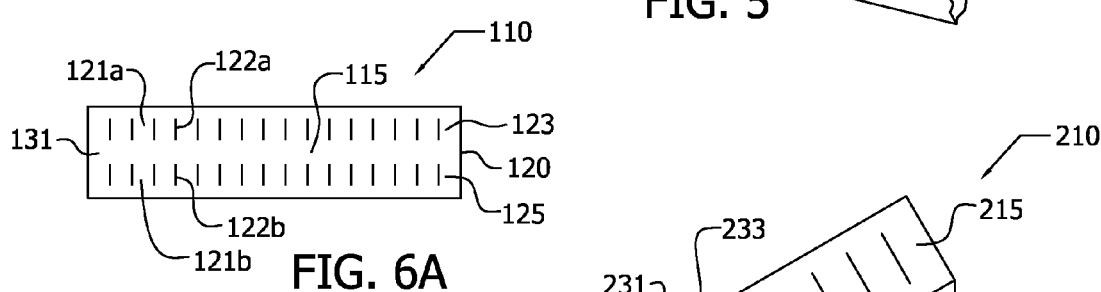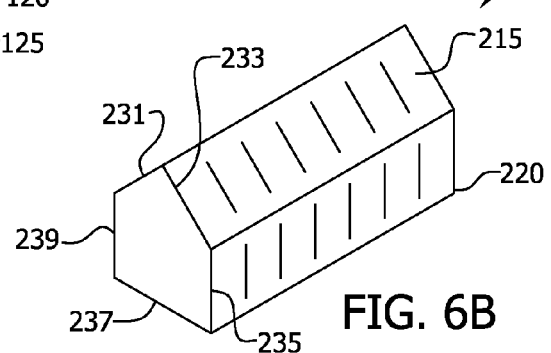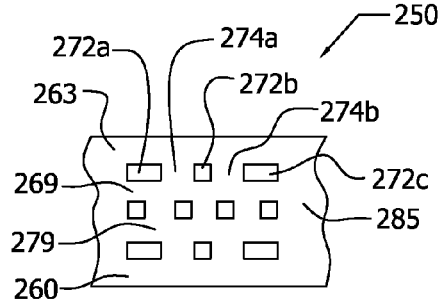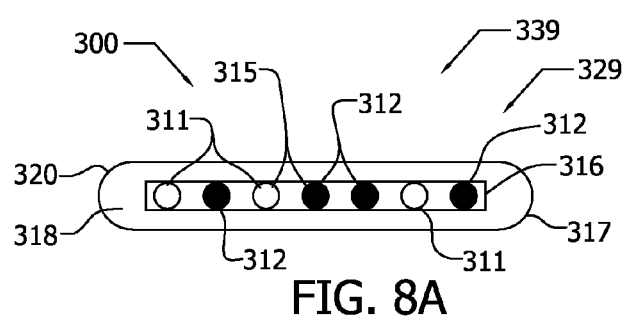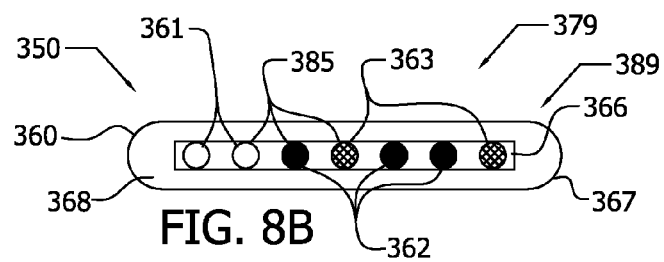

IMPLANTABLE IDENTIFICATION APPARATUS AND RELATED METHODS OF USE

CROSS-REFERENCE TO RELATED APPLICATION

The present application claims priority and benefit of U.S. Provisional Patent Application No. 61/979,736 filed Apr. 15, 2014, the disclosure of which is hereby incorporated by reference in its entirety herein.

BACKGROUND OF THE INVENTION

Field of the Invention

The present invention is directed to implantable personal identification devices and methods of accessing personal information associated therewith.

Background of the Invention

Implantable devices that provide personal information relative to the person having the implant are known. These devices frequently include a radio-frequency (RF) transmitter and are designed to be remotely scanned and can be used for a variety of purposes. For example, in the case of an unconscious or deceased individual, the implant can provide information relative to the identity of the individual. In the case of military personnel, the implant can provide identifying information and location for purposes of tracking troop movement. A problem with current implantable personal identification devices is that there is the possibility of unauthorized access to the implant's information. This may occur, for example, with the use of specialized detection equipment by someone in proximity to the implanted individual without the individual's knowledge. As a result, there are privacy concerns regarding the use of implantable personal identification devices. Furthermore there are health concerns due to the continued exposure of tissues surrounding the RF transmitter to electromagnetic radiation, and there may be other biocompatibility concerns with respect to the RF transmitter.

Accordingly, there is a need for an implantable personal identification device that cannot be remotely scanned, and a method for scanning an implanted personal identification device that requires the scanning equipment to be in physical contact with the implanted individual in immediate proximity to the implant in order for information to be extracted from the implant.

BRIEF SUMMARY OF THE INVENTION

These and other needs and disadvantages may be overcome by the apparatus and related methods and compositions of matter disclosed herein. Additional improvements and advantages may be recognized by those of ordinary skill in the art upon study of the present disclosure.

In various aspects the apparatus disclosed herein includes information linked to a person by data encoded in a texture. The texture has a pattern, and the texture is formed upon a side of a chip implantable within the person, in various aspects. The pattern may be resolvable by an ultrasound scanner into a pattern image that is computer readable to extract the data from the computer image when the chip is implanted within the person.

The related methods, in various aspects, include the step of encoding data upon a side of a chip by forming a pattern with a texture upon the side, the pattern resolvable into a pattern image by an ultrasound scanner when the chip is implanted within a body of a person, the data being linked to an identity of the person, and the step of implanting the chip within the body. The methods may include the step of obtaining a pattern image using the ultrasound scanner, the step of extracting data from the pattern image, and the step of displaying information linked to the person by the data encoded in the pattern, the information residing in a database accessible via the cloud.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

BRIEF DESCRIPTION OF THE DRAWINGS

FIG. 4 illustrates by cut-away side view the chip of the implantable identification apparatus of FIG. 1 passing through a cannula of a needle;

FIG. 5 illustrates by perspective view a slot being formed by a laser in portions of the chip of implantable identification apparatus of FIG. 1;

FIG. 6A illustrates by top view portions of a second exemplary implementation of an implantable identification apparatus;

FIG. 6B illustrates by perspective view portions of a third exemplary implementation of an implantable identification apparatus;

FIG. 7 illustrates by top view portions of a fourth exemplary implementation of an implantable identification apparatus;

FIG. 8A illustrates by top view portions of a fifth exemplary implementation of an implantable identification apparatus;

FIG. 8B illustrates by top view portions of a sixth exemplary implementation of an implantable identification apparatus; and, FIG. 9 illustrates by process flow chart exemplary methods of operation of an implantable identification apparatus.

Figure 1:
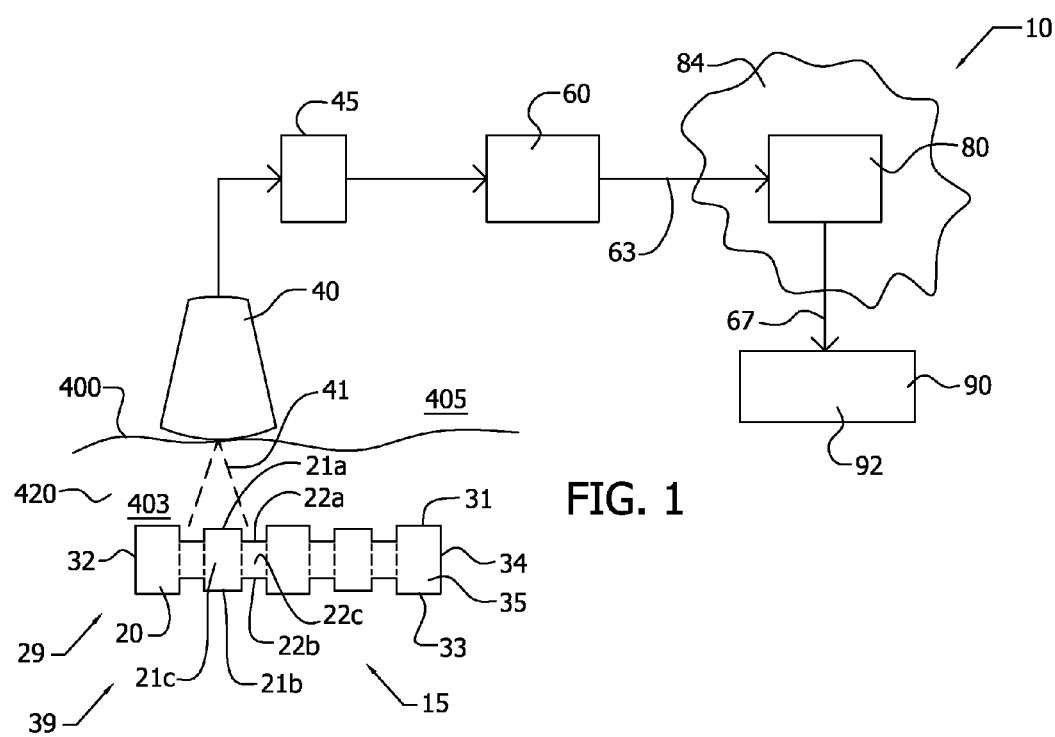
FIG. 1 illustrates in part by schematic diagram an exemplary implementation of an implantable identification apparatus.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

An implantable identification apparatus is disclosed herein along with related methods of use. The purpose of the implantable identification apparatus, in various aspects, is to provide identification of a person and allow access to information related to the person while protecting the person's privacy. The implantable identification apparatus, in various aspects, comprises a chip that may be implanted under the skin. The chip is made of non-magnetic, biologically compatible materials and has no moving parts, in various aspects. Data is encoded into a pattern formed by a physical structure of the chip. The pattern may be, for example, a texture on a surface of the chip or components having differing densities disposed about the chip. When the chip is implanted within a person, an ultrasound scanner may resolve the pattern into a pattern image that is computer readable. A computer may then read the pattern image and then extract data from the pattern image. The chip and the data encoded in the chip may be unique to the person. Using the data, information in a database may be accessed that may pertain to the person. The chip may not be read other than by direct contact with the person, emits no signals, and is MRI compatible.

In various aspects, the information may be medical records associated with the person. For example, each chip may be unique and may correspond to a unique person and uniquely correspond to the unique person's medical records, which may be stored electronically in the cloud. By scanning the implanted chip using an ultrasound scanner, medical providers may be linked to the person's medical records. The medical records may include, for example, chart notes, laboratory test results, radiographic images, surgical notes, diagnoses, or medical history. This may facilitate care of the person in the event the person is unable to communicate. The implantable identification apparatus disclosed herein has other possible applications, including employment and payroll tracking, security clearance, access control, control of equipment operation, immigration status, prisoner tracking, and military personnel identification.

The apparatus, methods, and compositions of matter disclosed herein may be generally implemented, at least in part, in software comprising computer readable instructions adapted to execute upon one or more computers to configure the one or more computers as the apparatus or to cause the one or more computers to perform the method steps. Software may be, for example, in the form of high-level code such as C or Java, or may be in the form of machine code. In some aspects, the software may execute on one computer. In other aspects, two or more computers may communicate with one another via network, and the software may be organized in various ways such that portions of the software may be distributed over the two or more computers to be executed by the two or more computers. The software may be configured into modules, and the modules may be organized in various ways in various aspects. Modules include routines, programs, components, data structures, etc., that perform particular tasks or implement particular abstract data types. The methods disclosed herein may be implemented in software, hardware, or combinations of software and hardware, in various aspects.

Computer, as used in this disclosure, includes a terminal that may have a computer screen, keyboard, and mouse, and is linked by network to a server. In such an aspect, various software, including software disclosed herein, may execute on the one or more processors in the server, and the computer screen provides a visual input/output interface from the server to the user. Computer further includes a computer with one or more processors, memory, computer screen(s), mouse, keyboard, storage device(s), and so forth. Computer further includes, for example, single-processor or multiprocessor computers, minicomputers, mainframe computers, as well as personal computers, hand-held computing devices, tablets, cellular telephones that include a processor, network hardware that comprises a processor (e.g. modems, routers, switches, satellite uplink/downlink transmitters and receivers, packet sniffers, or domain name servers), and processor-based or programmable consumer electronics. Computer may be cloud based at least in part, in various aspects. Computer screen includes one or more computer screens in communication with the computer that may be generally viewed by a user.

As used herein, the terms apparatus, component, and system may refer to a computer-related entity, either hardware, a combination of hardware and software, software operably received by a computer, or software in execution by a computer. For example, an apparatus may include a computer as well as various components of the computer such as a processor, memory, storage devices, computer screen, and communication interfaces (e.g. USB port, Ethernet port). Apparatus may include network communication hardware and software operably received by the network, in various implementations. Apparatus may include software in execution by a processor, an object, an executable, and a thread, in various implementations. One or more apparatus, in various implementations, may reside within a process and/or thread, and an apparatus may be localized on one computer, distributed between two or more computers, distributed over a network including the cloud.

The compositions of matter disclosed herein include non-transitory computer readable media that may be used to store computer readable instructions. The computer readable instructions stored by the computer readable media, when executed, cause a computer to perform various operations as directed by the computer readable instructions. Computer readable media may include, for example, RAM, ROM, EEPROM, flash memory or other memory technology, CD-ROM, digital videodisk (DVD) or other optical storage devices, magnetic cassettes, magnetic tape, magnetic disk storage, or other magnetic storage devices.

Network, as used herein, includes local area networks, wide area networks, the Internet (the cloud), and combinations thereof. Communication may be conducted over the network by various wired and wireless technologies and combinations thereof. Computers may be networked with one another, and storage, various input/output devices, servers, routers and suchlike may be provided about the network, as would be recognized by those of ordinary skill in the art upon study of this disclosure. As would be recognized by those of ordinary skill in the art upon study of this disclosure, the methods, apparatus, and compositions of matter disclosed herein may be practiced in distributed computing environments including local area networks, enterprise level networks, and the cloud.

FIG. 1 illustrates exemplary implantable identification apparatus 10. As illustrated in FIG. 1, implantable identification apparatus 10 includes chip 20, ultrasound scanner 40, computer 60, database 80, and display 92.

Figure 2:
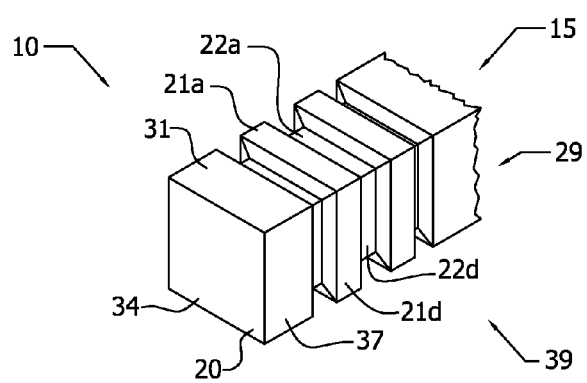
FIG. 2 illustrates by perspective view portions of the chip of the implantable identification apparatus of FIG. 1.

Chip 20 is illustrated as implanted in internal region 403 beneath skin 400 of person 420. Texture 15 on chip 20 forms pattern 29 that encodes data 39, and data 39 may be unique to person 420. Texture 15 is formed in the physical structural shape of chip 20, as illustrated. In this implementation, chip 20 is formed as a rectangular parallelepiped with elongated sides 31, 33, 35, 37, and rectangular ends 32, 34. Ridges, such as ridge 21a, and slots, such as slot 22a, are formed in side 31 of chip 20, and side 31 is oriented toward skin 400, as illustrated. Side 33, which is opposite of side 31 as illustrated, includes ridges, such as ridge 21b, that correspond to the ridges, such as ridge 21a, on side 31, and side 33 includes slots, such as slot 22b, that correspond to the slots, such as slot 22a, on side 31. Side 35, which is perpendicular to sides 31, 33, as illustrated, includes ridges, such as ridge 21c, that correspond to the ridges, such as ridge 21a, on side 31, and side 35 includes slots, such as slot 22c, that correspond to the slots, such as slot 22a, on side 31. As illustrated in FIG. 2, side 37 of chip 20, which is perpendicular to sides 31, 33, includes ridges, such as ridge 21d, that correspond to the ridges, such as ridge 21a, on side 31, and side 37 includes slots, such as slot 22d, that correspond to the slots, such as slot 22a, on side 31. Note that the ridges and slots span the width of side 37 between side 33 and side 31.

The ridges, such as ridges 21a, 21b, 21c, 21d, and slots, such as slots 22a, 22b, 22c, 22d, form texture 15 on the sides of chip 20 having pattern 29 that encodes data 39. Pattern 29 encodes data 39 in binary format, in this implementation, with either the ridges corresponding to 1's and the slots corresponding to 0's or vice versa. The same data 39 is encoded on all four sides 31, 33, 35, 37 of chip 20, in this implementation, because the same texture 15 with the same pattern 29 of ridges and slots is encoded on all four sides 31, 33, 35, 37. Thus, the orientation of chip 20 within internal region 403 does not matter as one of sides 31, 33, 35, 37 is oriented generally toward skin 400 to be resolved by ultrasound scanner 40, in this implementation. In other implementations, sides 31, 33, 35, 37 may have differing textures formed of slots and ridges, so that the pattern, such as pattern 29, and corresponding data, such as data 39, encompasses all of sides 31, 33, 35, 37. In still other implementations, sides 35, 37 may be of minimal thickness, less than the resolution of the ultrasound scanner 40 (for example 80 μm), so that no texture is formed on sides 35, 37 and, thus, no data is encoded on sides 35, 37.

As illustrated in FIG. 1, portions of ultrasound scanner 40 are biased against skin 400 in external region 405 to resolve the pattern 29 of texture 15, which includes slots, such as slot 22a, and ridges, such as ridge 21a, on chip 20. Ultrasound scanner 40 emits sound waves 41 that pass through skin 400 into internal region 403. The interaction of sound waves 41 with chip 20 resolves the pattern 29 into pattern image 45 of pattern 29 of ridges and slots (the texture 15) on side 31 of chip 20. In interacting with chip 20, the sound waves 41 may pass through chip 20, at least in part, or be reflected by chip 20, at least in part. Ultrasound scanner may include a processor and software operable to resolve pattern 29 into pattern image 45. Pattern image 45 includes a digital image of pattern 29, in various implementations. Pattern 29 of texture 15 is designed to be resolved by ultrasound scanner 40.

As illustrated in FIG. 1, pattern image 45 is transmitted from scanner 40 to computer 60, as illustrated, and computer 60 extracts the data 39 encoded in pattern image 45. Pattern image 45, as resolved by ultrasound scanner 40, is computer readable by computer 60. Using data 39, computer 60 accesses database 80 via network 63, and exemplary implantable identification apparatus 10 displays information 90 that is linked to person 420 by data 39. The communication of data 39 to database 80 may, at least in part, prompt the display of information 90. Information 90, as illustrated, is displayed by display 92, and information 90 may be communicated to display 92 via network 67. Information 90 may be in the cloud 84, in various implementations. Ultrasound scanner 40, computer 60, and display 92 may be generally a unitary assembly, or may be separate from one another and distributed over a room, a building, or over more remote geographic locals, in various implementations. Implantable identification apparatus 10 may include various computers for information management and display, displays, routers, network pathways, and other hardware and operable software, in various implementations, as would be readily understood by those of ordinary skill in the art upon study of this disclosure.

Chip 20 may be formed of one or more materials such as medical grades of silicone, poly-vinylchloride (PVC), poly-ethylene, PEEK, polycarbonate, ultem PEI, polysulfone, polypropylene and polyurethane that are biologically compatible for long-term implantation. In various implementations, chip 20 is passive in that there are no moving parts, no electronic components. In various implementations, chip 20 includes no metallic components, making chip 20 safe for use in the magnetic fields found proximate MRI scanners. Because chip 20 comprises bio-compatible materials, there are no concerns of tissue damage or tumor formation related to the device, as may be related, for example, to RFID devices. Furthermore, neither the presence of chip 20 nor data 39 encoded in pattern 29 of texture 15 can be detected remotely, in contrast with an RFID device including the data encoded by the RFID device.

Figure 3:
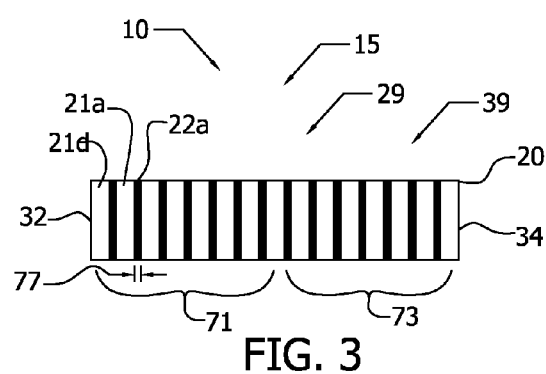
FIG. 3 illustrates by top view portions of the chip of the implantable identification apparatus of FIG. 1.

Ultrasound scanner 40 may have a resolution of about 80 μm, so the dimension of texture 15 are at least the resolution of ultrasound scanner or about 80 μm. For example, as illustrated in FIG. 3, the width 77 of slot 22a that represents a single binary bit may be about 100 μm, so that, for example, about 10 bits may be encoded per millimeter length of chip 20 or 100 bits per centimeter length of chip 20. The dimensions of texture 15 may be decreased as the resolution of ultrasound scanner 40 is increased.

As illustrated in FIG. 3, data 39 includes fields 71, 73. Field 71, for example, may uniquely identify the person 420. Communication of field 71 to database 80 may authorize, at least in part, access to information 90 associated with person 420. In various implementations, access to information 90 may be authorized only by communication of field 71 to database 80. Access to information 90 may be further controlled by various access controls such as passwords, biometrics, dongle, or encryption. For example, in a medical setting, information 90 may comprise medical records of person 420 as identified by field 71 and additional access controls may be imposed upon access to information 90. In various implementations, field 71 may verify that person 420 has access to information 90 and may be used to control the level of access of person 420 to information 90.

Field 73 may contain other information about person 420. In a medical setting, for example, field 73 may contain information indicative of a medical condition of person 420 such as blood type, organ donor status, medic alerts (e.g. diabetes, seizure disorders, allergies), emergency contacts, do not resuscitate (DNR) status, or life-threatening illnesses. Information from field 73 may be made available without additional access controls or without accessing database 80.

In various implementations, information 90 may be operative to control the access of person 420 to physical facilities such as secured facilities of various types. In various implementations, information 90 may be operative to control the operation of equipment by person 420 such as the ability to operate equipment or the operations that the person 420 is authorized to take with the equipment. In various implementations, information 90 may be augmented upon being accessed with field 71 to monitor the whereabouts of person 420 or the physical condition of person 420. Display 92 (see FIG. 1) may include a visual display, and display 92 may also include various I/O devices, access control of facility entrances and exits, communication devices, control of equipment, and so forth, to regulate the usage thereof by person 420 based, at least in part, upon field 71.

As illustrated in FIG. 4, chip 20 may be implanted into internal region 403 of person 420 through lumen 46 of cannula 43 and then through end 44 of cannula 43 that, for example, may be in communication with a syringe (not shown). Chip 20, as illustrated in FIG. 4, is surrounded by coating 25. Coating 25 may facilitate the passage of chip 20 through lumen 46 into internal region 403, and coating 25 may be comprised of a bio-absorbable material that dissolves following implantation within internal region 403. For example, coating 25 may be formed of glycerin.

FIG. 5 illustrates formation of slot 22c in side 35 of chip 20 by laser 105. Laser beam 107 from laser 105 machines material from chip 20 to form slot 22c, as illustrated. Laser 105 may be directed by computer to form slots, such as slot 22c, at the appropriate location leaving ridges at other locations along side 35 to form texture 15 having pattern 29, and thus encode the corresponding data, such as data 39, into chip 20. The laser 105 may be directed to form texture 15 to encode data 39 into chip 20 by various positioning apparatus that may be computer controlled to position chip 20 and laser 105 with respect to one another.

FIG. 6A illustrates exemplary implantable identification apparatus 110 that includes chip 120. As illustrated in FIG. 6A, chip 120 includes side 131 with texture 115 comprised of ridges, such as ridges 121a, 121b, and slots, such as slots 122a, 122b. The ridges and slots, in this implementation, are formed into rows 123, 125 disposed generally in parallel to one another along side 131. Ridge 121a and slot 122a are located in row 123 and ridge 121b and slot 122b are located in row 125. Rows 123, 125 differ from one another to effectively double the data encoded on side 131, in this implementation. The ridges and slots extend across only a portion of the width of side 131. Thus, multiple rows may be formed in side 131, in various implementations, as limited by the dimensions of side 131 and the resolution of the ultrasound scanner.

FIG. 6B illustrates exemplary implantable identification apparatus 210 including chip 220 that has a pentagonal cross-sectional shape. As illustrated in FIG. 6B, chip 220 includes sides 231, 233, 235, 237, 239 with texture 215 comprised of ridges and slots disposed thereupon to encode data. In some implementations, an ultrasound scanner, such as ultrasound scanner 40, may be capable of detecting the pattern of slots and ridges on all of sides 231, 233, 235, 237, 239 of chip 220 when chip 220 is implanted. Chips, such as chip 20, 120, 220, may have other geometric cross-sectional shapes (e.g. triangular, hexagonal, octagonal, or irregular) in other implementations, and data may be either inscribed or omitted from the various sides.

FIG. 7 illustrates exemplary implantable identification apparatus 250 including chip 260. A series of slots, such as slots 272a, 272b, 272c, interspaced with ridges, such as ridges 274a, 274b, are formed in side 263 of chip 260 to form texture 285 on side 263 having pattern 269 that encodes data 279. A laser, such as laser 105, may be used to form the slots. Note that the slots, such as slots 272a, 272b, 272c, are contained within side 263. The slots, such as slots 272a, 272b, 272c, are rectangular, as illustrated, but may be circular or have some other shape, in other implementations. The texture formed on the side of the chip may have a pattern such as a bar code or QR code, and the pattern may encode data in binary format, hexadecimal format, or other various other bases or formats, as would be recognized by those of ordinary skill in the art upon study of this disclosure. A laser may be used to form the texture on the side of the chip. The size of the texture, such as texture 285, is limited by the resolution of the ultrasound scanner or may be limited by attributes of the laser used to form the texture.

FIG. 8A illustrates portions of exemplary implantable identification apparatus 300 that includes chip 320 with components 315 having differing densities disposed about chip 320 in pattern 329 that encodes data 339. As illustrated in FIG. 8A, components 315 include lucent beads 311 (that may, for example, be formed of nylon) and opaque beads 312 (that may, for example, be formed of silicon). The lucent beads 311 and opaque beads 312 are arranged in pattern 329 to encode data 339, in this implementation. Objects that are highly reflective of sound waves, such as sound waves 41, are said to be opaque, while objects that allow sound waves to pass through with minimal reflection are lucent. The density of the lucent beads 311 differs from the density of the opaque beads 312, and an ultrasound scanner, such as ultrasound scanner 40, may detect the density difference to resolve the pattern 329 of the beads 311, 312 into a computer readable pattern image, such as pattern image 45. Opaque beads 312 may appear opaque in the pattern image, while lucent beads 311 may appear clear in the pattern image. Data 339 may then be extracted from the pattern image using a computer, such as computer 60. Lucent beads 311 absorb sound waves while opaque beads 312 reflect sound waves, so that the pattern 329 formed by the combination of lucent beads 311 and opaque beads 312 of chip 320 may be resolved by the ultrasound scanner, such as ultrasound scanner 40.

The implantable identification apparatus 350 illustrated in FIG. 8B includes chip 360. As illustrated, chip 360 includes components 385 comprising lucent beads 361, opaque beads 362, and semi-opaque beads 363 to form pattern 379 that encodes ternary data 389. The lucent beads 361, opaque beads 362, and semi-opaque beads 363 have different densities detectable by the ultrasound scanner to allow the ultrasound scanner to resolve pattern 379. Pattern 379 is a ternary code, in this implementation. Additional beads having varying degrees of opaqueness or lucentness may be included in other implementations, for example, to encode data in a quaternary, octal, or other base. Other non-binary codes may be implemented in other implementations. The lucent beads 311, 361, opaque beads 312, 362, or semi-opaque beads 363 may be fixed in a pattern, such as pattern 329, 379, by placing the beads in a sheath 316, 366, and that is then encased within case 317, 367, which may include a filler material 318, 368 such as a saline solution. The size of the lucent beads 311, 361, opaque beads 312, 362, and semi-opaque beads 363 may be dependent on the resolution capabilities of the ultrasound scanner employed for resolving the pattern of beads 311, 312 or the pattern of beads 361, 362, 363.

Figure 9:
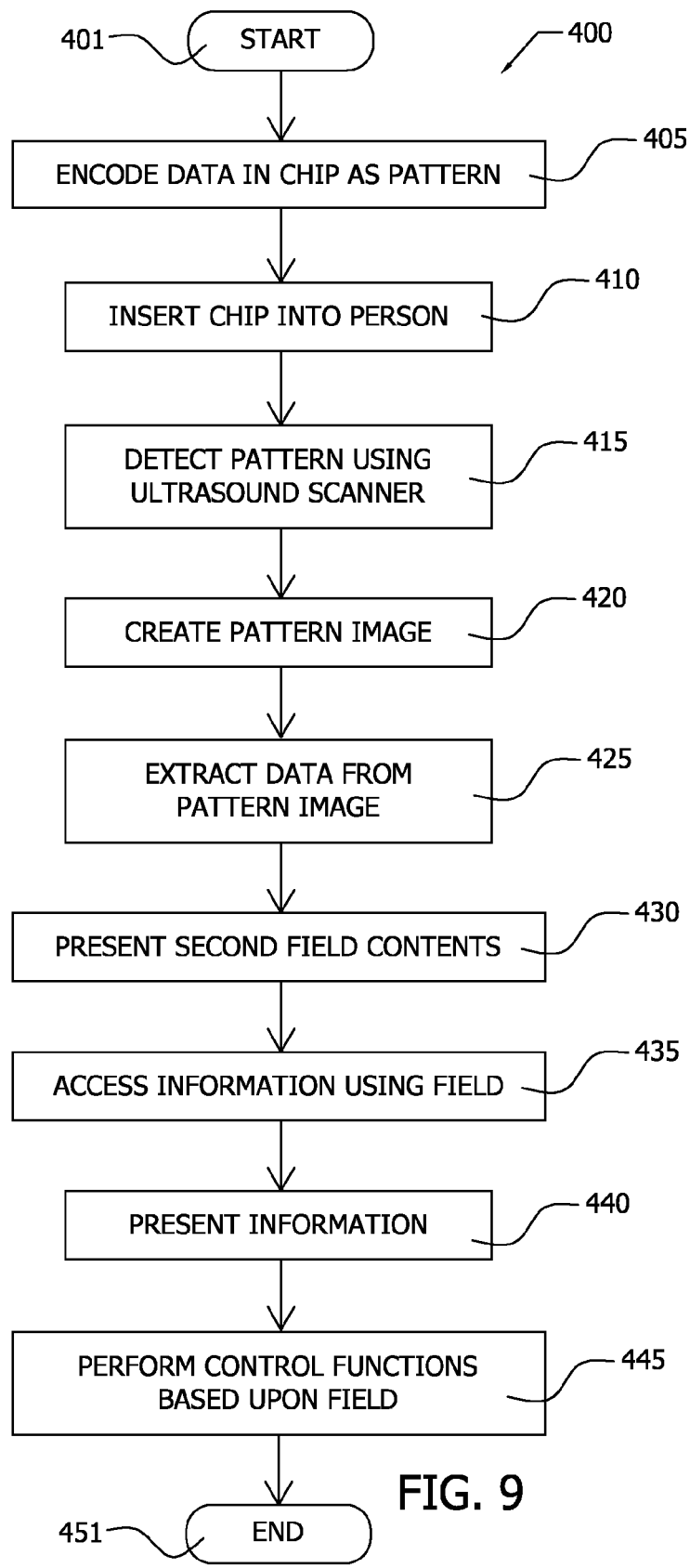

FIG. 9 illustrates exemplary method 400 of use of an identification apparatus, such as identification apparatus 10, 110, 210, 250, 300, 350. As illustrated in FIG. 9, method 400 is entered at step 401. At step 405, data, such as data 39, 279, 339, 389, is encoded by forming a texture, such as texture 15, 115, 215, 285, having a pattern, such as pattern 29, 269, 329, 379, on a chip, such as chip 20, 120, 220, 260, 320, 360. The pattern may encode data in binary format, ternary format, hexadecimal format. The texture may be formed on one or more sides of the chip. Data may be encoded on the chip using a laser, such as laser 105, to remove portions of the chip thereby forming slots, such as slots 22a, 22b, 22c, 22d, 122a, 122b, 272a, 272b, 272c, in the chip. Alternatively, data may be encoded in the chip by the arrangement of components having differing density about the chip. For example, by arranging beads such as beads 311, 312, 361, 362, 363 that are included in the chip. The data may comprise a field, such as field 71, that uniquely identifies the person, such as person 420, within whom the chip is to be implanted. Field 71 may be unique to person 420. The data may comprise a second field, such as field 73, that may contain information about the person that is open access-accessible without protection such as password, encryption, or other such access control.

At step 410, the chip is implanted in the person, for example, into internal region 403 beneath skin 400. The internal region may be generally proximate the skin to facilitate detection by an ultrasound scanner, such as ultrasound scanner 40. The chip may be implanted, for example, generally about the arm or other accessible place about the person. Placement of the chip may be generally standardized from person to person. That is, the chip may be implanted generally in the same location on each person to facilitate detecting the chip using the ultrasound scanner.

At step 415, the ultrasound scanner detects the chip including the pattern on the chip using sound waves, such as sound waves 41, and the ultrasound scanner resolves the pattern to create pattern image, such as pattern image 45, of the pattern, at step 420. The pattern image is computer readable.

The data is extracted from the pattern image, at step 425 using a computer, such as computer 60. The contents of the second field are presented at step 430, using, for example, a display, such as display 92. The computer may control the display, in various implementations.

At step 435, data from the field is used by the computer to accesses a database, such as database 80, via a network, such as network 63. Data from the field may associate information in the database with the person, and at least some of the information may be unique to the person. Information, such as information 90 may be communicated from the database to the display via a network, such as network 67, for display by the display. The data from the field may be required in order to access the database including the information. The networks, such as networks 63, 67, may encompass the cloud, in various implementations.

At step 445, various control or data functions may be allowed or disallowed based upon the field, which may be indicative of the identity of the person. The date, time, and location of the acquisition of the data may be logged into the database. Based upon the identity of the person as determined from the field, the person, for example, may be allowed to perform various actions such as access a specific facility, operate specific equipment, or operate specific equipment in specified ways. Method 400 terminates at step 451.

The foregoing discussion along with the Figures discloses and describes various exemplary implementations. These implementations are not meant to limit the scope of coverage, but, instead, to assist in understanding the context of the language used in this specification and in the claims. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. An implantable identification apparatus, comprising a chip implantable within a body of a person, the chip comprising a pattern that encodes data, the pattern formed by a texture of a side of the chip, the pattern resolvable into a pattern image by an ultrasound scanner when the chip is implanted within the body, wherein the texture comprises a plurality of ridges and a plurality of slots.

2. The apparatus of claim 1, further comprising a computer operably linked to the ultrasound scanner to extract data from the pattern image, the computer in communication with a database to display information from the database linked to the person by the data.

3. The apparatus of claim 1, further comprising information linked to the person by the data encoded in the pattern.

4. The apparatus of claim 3, wherein the information comprises medical records of the person.

5. The apparatus of claim 3, wherein at least a portion of the information resides in a database accessible via the cloud.

6. The apparatus of claim 1, a portion of the data indicative of a medical condition of the person.

7. The apparatus of claim 1, the chip sized for implantation into the body through a lumen of a cannula.

8. The apparatus of claim 1, wherein the plurality of ridges and the plurality of slots are formed into rows disposed in parallel to each other along the side of the chip.

9. An implantable identification apparatus, comprising a chip implantable within a body of a person, the chip sized for implantation into the body through a lumen of a cannula, the chip comprising a pattern that encodes data, the pattern resolvable into a pattern image by an ultrasound scanner when the chip is implanted within the body, wherein the apparatus further comprises a coating that surrounds the chip to facilitate passage of the chip through the lumen into the body, the coating dissolvable within the body.

10. An implantable identification apparatus, comprising a chip implantable within a body of a person, the chip comprising a pattern that encodes data, the pattern resolvable into a pattern image by an ultrasound scanner when the chip is implanted within the body, the chip formed as a rectangular parallelepiped, the pattern on each of the four elongate sides of the chip being the same.

11. An implantable identification apparatus, comprising a chip implantable within a body of a person, the chip comprising a pattern that encodes data, the pattern formed by components having different densities disposed about the chip, the pattern resolvable into a pattern image by an ultrasound scanner when the chip is implanted within the body, wherein the components comprise a plurality of opaque beads and a plurality of lucent beads, the opaque beads and lucent beads arranged to encode binary data.

12. The apparatus of claim 11, wherein the opaque beads are formed of silicon and the lucent beads are formed of nylon.

13. The apparatus of claim 11, wherein the components further comprise a plurality of semi-opaque beads, the opaque beads, lucent beads and semi-opaque beads arranged to encode ternary data.

* * * * *